United States Patent
Frey et al.

(10) Patent No.: US 7,670,846 B2
(45) Date of Patent: Mar. 2, 2010

(54) AUTOMATIC DIFFERENTIATION OF A SAMPLE SOLUTION AND A CONTROL SOLUTION

(75) Inventors: Guenter Frey, Ellerstadt (DE); Carina Horn, Biblis (DE); Otto Gaa, Worms (DE); Hans Kintzig, Tiefenthal (DE); Hans-Ruediger Murawski, Lampertheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1332 days.

(21) Appl. No.: 10/518,968

(22) PCT Filed: Jun. 24, 2003

(86) PCT No.: PCT/EP03/06613

§ 371 (c)(1),
(2), (4) Date: Dec. 21, 2004

(87) PCT Pub. No.: WO2004/003549

PCT Pub. Date: Jan. 8, 2004

(65) Prior Publication Data

US 2005/0244981 A1    Nov. 3, 2005

(30) Foreign Application Priority Data

Jun. 29, 2002   (DE)   ................ 102 29 314

(51) Int. Cl.
*G01N 21/17*   (2006.01)
*G01N 21/27*   (2006.01)

(52) U.S. Cl. ............... 436/164; 436/8; 436/16; 436/166; 436/171; 436/174; 422/82.05; 422/82.09; 356/51; 356/317; 356/432; 356/436; 356/441

(58) Field of Classification Search ............. 436/8, 436/13, 14, 16, 164, 166, 171, 174; 422/82.05, 422/82.09; 356/51, 300, 317, 318, 319, 432, 356/436, 441, 442

See application file for complete search history.

(56) References Cited

U.S. PATENT DOCUMENTS

| 3,920,580 | A | * | 11/1975 | Mast | ............................. 436/14 |
|---|---|---|---|---|---|
| 4,399,362 | A | | 8/1983 | Cormier et al. | |
| 5,187,100 | A | | 2/1993 | Matzinger et al. | |
| 5,605,837 | A | | 2/1997 | Karimi et al. | |
| 5,958,780 | A | | 9/1999 | Asher et al. | |
| 6,080,583 | A | | 6/2000 | Von Bahr | |
| 6,824,670 | B2 | | 11/2004 | Tokunaga et al. | |
| 6,900,058 | B2 | * | 5/2005 | Rannikko et al. | .............. 436/14 |
| 2002/0139692 | A1 | | 10/2002 | Tokunaga et al. | |
| 2002/0160517 | A1 | * | 10/2002 | Modzelewski et al. | ........ 436/44 |
| 2003/0036202 | A1 | * | 2/2003 | Teodorcyzk et al. | .......... 436/63 |
| 2007/0256943 | A1 | | 11/2007 | Popovich et al. | |

FOREIGN PATENT DOCUMENTS

| DE | 19821903 | | 1/1999 |
|---|---|---|---|
| EP | 0 132 399 A1 | | 1/1985 |
| EP | 1 156 324 A1 | | 11/2001 |
| EP | 0 800 086 B1 | | 1/2003 |
| JP | 1035374 | | 2/1989 |
| JP | 5099930 | | 4/1993 |
| WO | WO 89/09931 A1 | | 10/1989 |
| WO | 2006/065899 | * | 6/2006 |

OTHER PUBLICATIONS

M. Matsuoka, "Infrared Absorbing Dyes," Plenum Press, New York (1990).
German Search Report mailed on Jul. 13, 2009 (2 pgs).

* cited by examiner

*Primary Examiner*—Maureen M Wallenhorst
(74) *Attorney, Agent, or Firm*—Woodard, Emhardt, Moriarty, McNett & Henry LLP

(57) ABSTRACT

The invention concerns a method for automatically differentiating between a sample liquid and a control liquid especially within the context of analytical measuring systems, wherein the presence of a special property of the control liquid and/or at least two criteria are used for the differentiation. In addition the invention concerns appropriate control liquids that are suitable for the new method.

7 Claims, 1 Drawing Sheet

AUTOMATIC DIFFERENTIATION OF A SAMPLE SOLUTION AND A CONTROL SOLUTION

The invention concerns a method for automatically differentiating between a sample liquid and a control liquid especially within the context of analytical measuring systems. The invention also concerns appropriate control liquids that are suitable for the method.

Monitoring of body functions by determining the content of individual, usually low molecular weight metabolites in body fluids has become an indispensable instrument of modern medicine. Prominent examples are blood sugar self-monitoring by diabetics and recently, to an increasing extent, the measurement of the blood cholesterol content and lactate concentration in blood where the latter is used especially in sport medicine to check individual fitness.

Numerous test strips are now commonly used for the reliable, rapid and uncomplicated analysis of body fluids and in particular blood and urine. Simple test strips allow a visual determination of the concentration of the analyte of interest for example by means of colour changes of a reagent layer on the test strip and comparison with a colour scale which in turn correlate with analyte concentrations. Measuring systems which comprise test strips as well as measuring instruments are more convenient. These systems detect the changes, usually photometrically or electrochemically, which occur when the analyte reacts with the reagents that are present on or in the test strip.

Since test strips cannot be manufactured in one hundred percent identical lots, it is necessary to calibrate the measuring instrument in a lot-specific manner. This is nowadays carried out automatically by means of lot-specific codes which are read by the measuring instrument or are entered into the measuring instrument by the user and which automatically adjust an algorithm for evaluating the measured values.

In addition to the lot-specific differences which are due to the manufacturing process, test strips and also measuring instruments are subject to variations in their measuring accuracy and reliability which for example may be caused by long or inappropriate storage of the test strips or maybe due to usage in the case of measuring instruments. Hence it is necessary to carry out a functional and quality control of the measuring system at regular intervals in order to detect and, if necessary, eliminate errors in a timely manner. For these purposes manufacturers of measuring systems offer control liquids which are in each case specific for a measuring system. The control liquids are usually essentially composed of aqueous, buffered solutions of the analyte in a known, predetermined concentration. They may also, however, contain other additives which for example imitate as accurately as possible the viscosity or colour of the actual sample liquid with the purpose of simulating measuring conditions as realistically as possible. Such control liquids are known for example from U.S. Pat. No. 5,187,100 and U.S. Pat. No. 5,605,837.

A control liquid is described in U.S. Pat. No. 5,187,100 which was designed for blood glucose measurement using the One-Touch™ System of Lifescan Inc.. The One-Touch™ System is an optical measuring system based on a two wavelength measurement at 635 nm and 700 nm consisting of a measuring instrument and test strips. The control liquid from U.S. Pat. No. 5,187,100 essentially simulates the flow properties of whole blood which is why it is designed as a two phase dispersion of deformable, non-water-soluble polymer particles in water to which a predetermined amount of glucose is added. In addition to other ingredients, the addition of a dye, copper phthalocyaninetetrasulfonic acid, tetrasodium salt is also mentioned for the control liquid from U.S. Pat. No. 5,187,100 as a so-called offset adjuster. However, this document does not address the fact that a differentiation between sample and control liquid by the instrument may be important. On the contrary the purpose of the described control liquid is to reduce as far as possible the differences between sample and control liquids.

U.S. Pat. No. 5,605,837 describes control liquids which are intended for use with the SURESTEP™ System of Lifescan Inc. The SURESTEP™ System is also an optical two wavelength measuring system for blood glucose measurements which detects at 660 nm and 940 nm and also comprises a measuring instrument and test strips. Whereas the increase in dye formation on the test strip when glucose is present in the sample liquid is detected at 660 nm, the measurement at 940 nm is used to check that blood is present on the test strip in an adequate amount. In order to ensure the latter function also for the control liquid, the control liquid is coloured with opaque particles, for example carbon or iron oxide, so that an absorbance can be observed at 940 nm. This document also does not describe a procedure which would enable a measuring instrument to automatically differentiate between a sample and control liquid.

EP-A 0 800 086 (Bayer) describes control liquids for electrochemical measuring systems which allow the control liquid to be detected and distinguished from a sample by the instrument; in this procedure measured values which are derived from a determination of a control liquid are preferably not admitted into the store of measured values. EP-A 0 800 086 proposes an algorithm which takes into consideration the dynamic current time course of the sample and control liquid measurement. However, this method is not transferable to measuring systems (such as photometric systems) other than electrochemical systems. Moreover the differentiation described in EP-A 0 800 086 requires that a ratio is formed between a read current and a burn current.

Hence there is a need for a method and corresponding control liquids which can be used with optical and/or electrochemical measuring systems to enable an automatic differentiation between sample and control liquid.

The object of the present invention was to eliminate the disadvantages of the prior art.

This is achieved by the subject matter of the invention as characterized in the independent patent claims. Preferred embodiments of the invention are defined in the dependent patent claims.

The invention concerns a method for automatically differentiating between a sample liquid and a control liquid with the aid of an analytical measuring system which detects a special property of the control liquid or the automatic differentiation is carried out on the basis of at least two criteria which relate to the property of the sample liquid or the control liquid detected by the measuring system.

The quality and/or functional control of an analytical system which consists of test elements (also referred to synonymously as test strips) and a measuring instrument should ensure that measured results that are obtained in a measurement with the analytical system are always correct, accurate and repeatable. These are indispensable prerequisites for reliably excluding erroneous diagnoses or treatments especially for medical diagnostics that should give the doctor indications for a targeted therapy.

According to the invention the analytical measuring system comprises test elements and accompanying measuring instruments.

The measuring system preferably comprises test elements (which are often also referred to synonymously as test strips or test devices) that can be evaluated photometrically and a photometer. In this preferred embodiment an optically detectable property of the sample or control liquid is detected and evaluated by the measuring system e.g. absorption, transmission, remission, fluorescence or phosphorescence etc..

Alternatively it is preferred according to the invention that the measuring system comprises test elements (often also referred to as test strips, test devices or sensors) that can be evaluated electrochemically and an electrochemical measuring instrument. Electrochemical properties that can be detected and evaluated by such systems include voltages (e.g. in potentiometry), currents (in amperometry or voltammetry), charges (e.g. in coulometry) etc..

Test elements in the sense of the invention comprise specific reagents for one or more analytes in a detection system. When the analyte is present in the sample liquid, the detection system results in a signal that can be detected by the measuring instrument of the measuring system which is for example caused by a colour formation or a characteristic current. Numerous embodiments of suitable test elements and detection systems are known to a person skilled in the art. For example the detection system can contain an enzyme, an electron carrier and an indicator dye.

The method according to the invention essentially uses an aqueous solution of the target analyte, for example glucose, cholesterol or lactate as control liquids. The target analyte is preferably present in the solution in a predetermined, known concentration. Common additives such as buffer substances, stabilizers, inorganic salts etc. may be added to this solution. When selecting the additives, care only has to be taken that they do not affect and in particular do not interfere with the desired detection reaction of the test strip. For example in the case of optical detection systems, the additives should not have any effect on the colour development of the indicator substance. This applies similarly to electrochemical detection systems or enzymatic reactions which occur on the test strip.

First Embodiment

Figure 1:
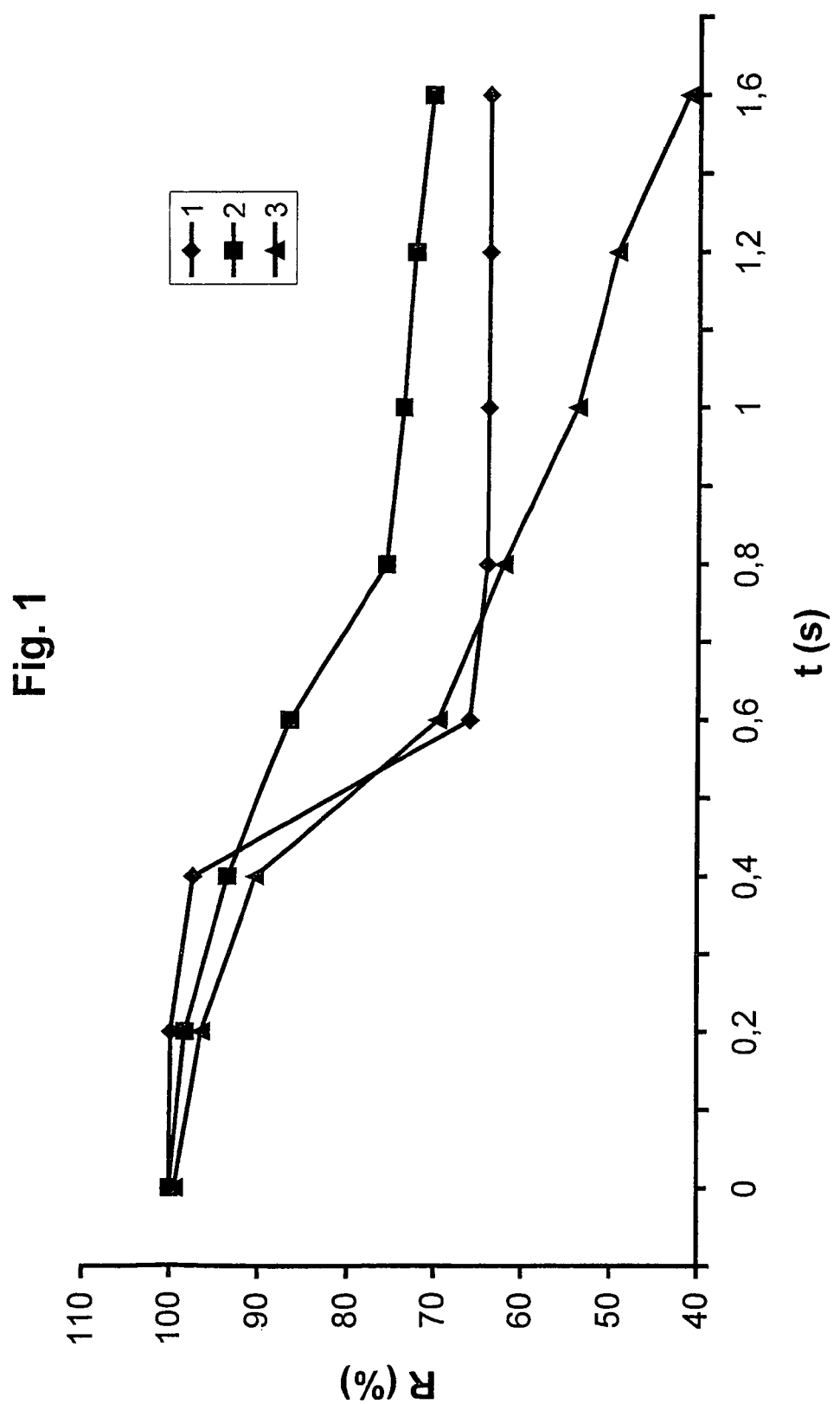
FIG. 1 is a plot of relative remission versus time for blood samples and control liquids.

According to the invention it is preferred that the automatic differentiation between sample and control liquid is based on a special property of the control liquid which the sample liquid does not have or to a different degree. This may be an optically or electrochemically detectable property, in particular absorption, remission or conductivity (e.g. different salt content of the control solution compared to the sample liquid) or flow behaviour (e.g. an aqueous control solution can fill a capillary more rapidly than a blood sample).

This special property is preferably caused by a substance added to the control liquid which preferably does not occur in the sample liquid.

In the case of photometric measuring systems it is preferred that a dye is added to the control liquid. It is particularly preferred that the added dye is an IR dye which does not have any significant absorption in the wavelength range in which the measurement signal for the analyte determination is detected. Dyes have turned out to be particularly suitable according to the invention which absorb in the near infrared range (so-called IR dyes). For example the following classes of compounds have proven to be suitable: metal complexes of quinolinequinones, nickel dithiolene dyes, nickel tetramine dyes, quinone dyes, phthalocyanine dyes, naphthocyanine dyes, special azo dyes (cf. M. Matsuoka, Infrared absorbing dyes, Plenum Press, New York, 1990). The following IR dye has proven to be especially preferable ST 1651 (2-[2-[2-chloro-3-[[1,3-dihydro-1,1-dimethyl-3-(4-sulfobutyl)-2H-benz[e]indol-2-ylidene]-1-cyclopentene-1-yl]ethenyl]-1,1-dimethyl-3-(4-sulfobutyl)-1H-benz[e]indolium, internal salt, sodium salt) which can for example be obtained from SYNTHON Chemie GmbH&Co.KG Company, Wolfen, Germany.

In the case of electrochemical measuring systems it is preferred that the substance added to the control liquid is electrochemically active. In particular it has been proven to be advantageous according to the invention when the added substance is an electrolyte (e.g. sodium chloride etc.) which clearly changes the conductivity of the control solution in comparison to blood, plasma, serum or other body fluids. The greatly increased conductivity of the control solutions compared to isotonic body fluids is used for the differentiation (control sample/measurement solution) in the measuring instrument. For example an appropriate reading is triggered in the display on the basis of the conductivity thresholds specified for the instrument or an entry is made in the store of measured values which identifies the measurement as a measurement of a control solution.

In another embodiment a substance is added to the control solution which is electrochemically inactive i.e. it has no effect on the measured signal and is only used to delay the flow properties of the control solution (for example preferably in a test device capillary). The filling time of the measurement solution that flows into the capillary is determined by a two point measurement (e.g. by the conductivity or impedance). If the time exceeds the specifications for physiological solutions (blood, plasma, serum, liquor etc.), then it is a control solution which is recognized and identified as such by the measuring instrument. Preferred additives are thickening agents (for example derivatives of alginic acid; cellulose derivatives; swelling agents).

In a particularly preferred embodiment of the invention the substance added to the control liquid does not have an effect on the detection system of the analytical measuring system. Measurement of the control liquid by the analytical measuring system is used to monitor the properties of the measuring system and of the detection system. For this purpose the control liquid usually contains a known amount of analyte. This amount is determined with the aid of the detection system. The presence of additional substances in the control liquid should not change the reactions in the detection system and the processes in the measuring system to such an extent that different measuring results are obtained in the sample liquid and in the control liquid for the same analyte concentrations.

The substance or substances that are added to the control liquid used according to the invention should, according to the invention, not interfere with or not have a significant effect on the actual measuring process in order to allow an identification of the control liquid. For optical measuring systems this means that the added substance has an absorption spectrum but has no absorption at the detection wavelength of the measuring system. In the case of electrochemical measuring systems care must be taken that the added substance cannot interfere with the electrochemical measuring process due to its redox properties. For example the redox potential of the added substance should not be at such a level that it is converted at the electrodes when the detection voltage is applied to an amperometric sensor system and thus result in a flow of current. Furthermore the added substances should not affect the detection reaction in a manner described above for additives.

According to the invention a method is preferred in which the criteria for differentiating between sample and control liquid is based on different wetting properties of the control liquid and sample liquid. A method is particularly preferred in which the rate of wetting is used as a criterion to differentiate between sample liquid and control liquid.

Second Embodiment

Furthermore within the scope of the present invention a differentiation is proposed in which two criteria are used to differentiate between samples and control liquid. Such a method according to the second embodiment can be carried out without the control liquid having a property that is absent in the sample liquid. Rather the differentiation is based on a different magnitude of a common property. However, a property which the sample liquid does not have or has in a different form can additionally be used for the differentiation. According to the description of the first embodiment this additional property can be generated by adding substances to, the control liquid.

It was found that the property of a sample measured by the analytical measuring system develops differently over time than when a control liquid is measured. In particular it was found that the measured signal for the control liquid more rapidly approaches an end value and the end value is more constant than with a natural sample e.g. a blood sample.

For example in the context of optical measuring systems it has turned out that a considerably higher decrease in remission is observed when using a control liquid than when using sample liquids in particular blood which very rapidly leads to stable remission values. More details on this are described in example 1. Following example 1 it is especially preferred according to the invention that a control solution containing an IR dye is used in a photometric test system comprising photometric test elements and a photometer and that blood is used as the sample liquid and a photometer measures the absorbance or remission in the IR range.

Alternatively it is preferred that in an electrochemical test system comprising test elements that are evaluated electrochemically and an electrochemical measuring instrument, a control solution containing an electrochemically active additive is used and blood is used as the sample liquid, and the electrochemical measuring instrument differentiates between the control solution and the sample liquid by detecting the respective conductivities or viscosities. Also in this case it was found that the measured signal of the control liquid more rapidly approaches an end value than with a sample liquid and that the end value is more constant.

On the basis of these observations a method is proposed in which the time course of the measured values is recorded after applying the sample or control liquid and the time course is evaluated with regard to how rapidly the measured value approaches an end value and the constancy of the end value is also determined. FIG. 1 shows typical signal time courses. For the control liquid an initial phase is seen in which there are large erratic changes in the signal and an end phase with essentially constant measured values which reflect an end value. In order to differentiate between a sample and control liquid the time range can be determined in which a certain signal amplitude occurs and the respective range can be detected as an initial phase. Furthermore the end point or an end phase can be detected using a termination criterion. Possible termination criteria are for example a change in signal of less than a specified differential value or several measured values which fluctuate around a mean by less than a specific value. The time period of the initial phase or the rate of a signal change can be used as a first criterion. The variation of measured values in the end phase or the change of measured values over time in the end phase can be used as a second criterion. The variation can for example be determined by a summation of deviations from a mean or by determining the standard deviation. A short initial phase and a high constancy of the measured values in the end phase is particularly pronounced when the measured values are determined on the basis of a special property of the control liquid for example by an added substance. The concentration of this substance is preferably essentially constant during the measurement. A rapid and reliable detection is ensured by adapting a measurement to the special property. This results in a short initial phase and a higher constancy of the measured values in the end phase. An appropriate adaptation can for example be achieved by a dye in the control liquid and a detection unit which specifically measures the absorption of the dye.

Another subject matter of the invention according to the first or second embodiment is a control liquid which is suitable for use in the method according to the invention. For this purpose the control liquid advantageously contains an electrochemically active substance and/or a dye where the substance and/or the dye do not have an effect on the detection system of the measuring system. It is especially preferred that the control liquid contains an IR dye as described above.

The invention is further elucidated by the following example:

EXAMPLE 1

Blood samples and control liquids were measured by reflection photometry at 880 nm using the photometric blood glucose test strips AccuCheck® Compact from Roche Diagnostics GmbH, Mannheim, Germany. The remission was measured in 0.2 s steps.

Commercially available AccuCheck® Compact Control was used as the control liquid to which 3 mg/g solution of the IR dye ST 1651 (2-[2-[2-chloro-3-[[1,3-dihydro-1,1-dimethyl-3-(4-sulfobutyl)-2H-benz[e]indol-2-ylidene]-1-cyclopentene-1-yl]ethenyl]-1,1-dimethyl-3-(4-sulfobutyl)-1H-benz[e]indolium, internal salt, sodium salt) which can for example be obtained from SYNTHON Chemie GmbH&Co.KG Company, Wolfen, Germany was added.

A typical time course of the remission (relative remission R) versus time t (in s) is shown in FIG. 1. It can be clearly seen that the blood samples (2 and 3) lead much more slowly to a decrease in remission than the control solution (1) and that the remission does not reach a stable end value within the measured time window.

The following criteria have proven to be suitable in this example for identifying the control liquid:

1.) The difference in the measured values between the wetted and unwetted test field must be 25% or more (expressed in terms of relative remission, "rel. rem.") and at the same time 2.) the difference in the measured value of the completely wetted test field compared to that of the directly subsequent measurement cycle must be 7% relative rem. or less.

Only control liquids simultaneously fulfil these two criteria; blood samples always have a different wetting behaviour which is exhibited by the fact that at least one of the abovementioned criteria is not met.

The invention claimed is:

1. A method for automatically determining whether a sample liquid to be tested in an optical measuring instrument is a test sample or a control sample; comprising:
   (a) providing an optical measuring instrument effective for measuring sample liquids for an analyte of interest, wherein each of said sample liquids may be a test sample or a control sample;
   (b) providing one or more control samples containing a known concentration of said analyte of interest, wherein each of said control samples has been provided with a special optical property that is not present in any of said test samples;
   (c) using said optical measuring instrument to measure one of said sample liquids for the analyte of interest, wherein the optical measurement additionally evaluates said special optical property; and
   (d) automatically determining whether the measured sample liquid is a control sample or a test sample by causing the optical measuring instrument to identify the results of the evaluation of said special optical property as being consistent with either a control sample or a test sample;
   wherein said using said optical measuring instrument comprises using a photometer to measure absorption or remission in the IR range; wherein said special optical property is provided by providing a dye in the control sample; and wherein the dye is an IR dye which does not have a substantial absorption in the wavelength range in which the measurement signal for the analyte of interest is detected.

2. A method according to claim 1 wherein the dye is a member selected from the group consisting of metal complexes of quinolinequinones, nickel dithiolene dyes, nickel tetramine dyes, quinone dyes, phthalocyanine dyes, naphthocyanine dyes, and azo dyes.

3. A method according to claim 1 wherein the dye is (2-[2-[2-chloro-3-[[1,3-dihydro-1,1-dimethyl-3-(4-sulfobutyl)-2H-benz[e]indol-2ylidene[-1- cyclopentene-1yl[ethenyl]-1,1-dimethyl-3-(4-sulfobutyl)-1H-benz[e]indolium, internal salt, sodium salt.

4. A method according to claim 1 wherein said special optical property is a higher decrease in remission in comparison to the decrease in remission typically observed in a test sample.

5. A method according to claim 1 wherein said optical measuring instrument evaluates two or more properties in the measured sample liquid, wherein said two or more properties, in combination, have been identified as being indicative of either a control sample or a test sample; and further wherein said automatically determining step includes causing the measuring instrument to identify the results of the evaluation of said two or more properties as being consistent with either a control sample or a test sample.

6. A method according to claim 5 wherein one of said two or more properties is an optical property.

7. A method for automatically determining whether a sample liquid to be tested in an optical measuring instrument is a test sample or a control sample; comprising:
   (a) providing a photometer effective for measuring sample liquids for an analyte of interest, wherein each of said sample liquids may be a test sample or a control sample;
   (b) providing one or more control samples containing a known concentration of said analyte of interest, wherein each of said control samples has been provided with an IR dye that is not present in any of said test samples, wherein the IR dye does not have a substantial absorption in the wavelength range in which a measurement signal for the analyte of interest is detected;
   (c) using said photometer to measure one of said sample liquids for the analyte of interest, and additionally using said photometer to measure absorption or remission in the IR range; and
   (d) automatically determining whether the measured sample liquid is a control sample or a test sample by causing the photometer to identify the results of the measurement of absorption or remission in the IR range as being consistent with either a control sample or a test sample.

* * * * *